United States Patent [19]
El-Hage et al.

[11] Patent Number: 5,964,381
[45] Date of Patent: Oct. 12, 1999

[54] DEVICE FOR PROJECTILE DISPENSING OF SMALL VOLUME LIQUID SAMPLES

[75] Inventors: Amer El-Hage, Menlo Park; Joseph Leytes, Moutain View, both of Calif.

[73] Assignee: LJL BioSystems, Inc., Sunnyvale, Calif.

[21] Appl. No.: 08/968,657

[22] Filed: Nov. 12, 1997

[51] Int. Cl.⁶ .............. B67D 5/42; B67D 5/52; B65D 5/72
[52] U.S. Cl. .......... 222/386; 222/135; 222/149; 222/389; 222/571
[58] Field of Search .................. 222/386, 389, 222/149, 571, 383.1, 135, 129, 130

[56] References Cited

U.S. PATENT DOCUMENTS

| | | | |
|---|---|---|---|
| 3,851,798 | 12/1974 | Miller | 222/135 |
| 3,934,585 | 1/1976 | Maurice | 128/225 |
| 4,363,429 | 12/1982 | Schindler | 222/504 |
| 5,252,037 | 10/1993 | Carlson | 417/339 |
| 5,525,302 | 6/1996 | Astle | 422/100 |

Primary Examiner—Andres Kashnikow
Assistant Examiner—Keats Quinalty
Attorney, Agent, or Firm—Kolisch, Hartwell, Dickinson, McCormack & Heuser

[57] ABSTRACT

A piston is disposed inside a tube having an inner cross sectional size and shape uniform along its length. The tube has an open end. The piston is free to move linearly inside the tube and preferably may move out of the tube through the open end. If the tube is cylindrical, for example, it has a constant inner diameter. The open end of the tube is neither tapered or flaring. Liquid samples are aspirated into the device by pulling the piston back. The sample is then ejected by accelerating the piston to a minimum velocity to force the liquid sample out of the open end of the tube. The velocity of the sample is sufficient to render negligible the effects of surface tension forces. The volume of the liquid sample dispensed is determined by the inner diameter of the tube and the piston displacement. Accurate positioning of the piston provides samples of accurate volumes. A specific embodiment of the present invention uses a tube with an inner diameter of 0.5 mm, resulting in a volume displacement of 1.9 microliters per centimeter of piston travel.

26 Claims, 7 Drawing Sheets

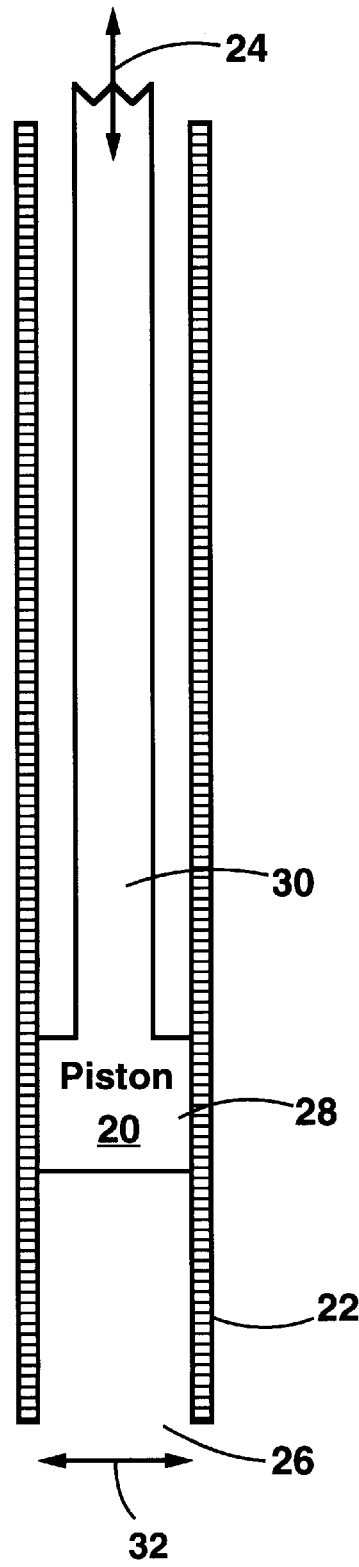
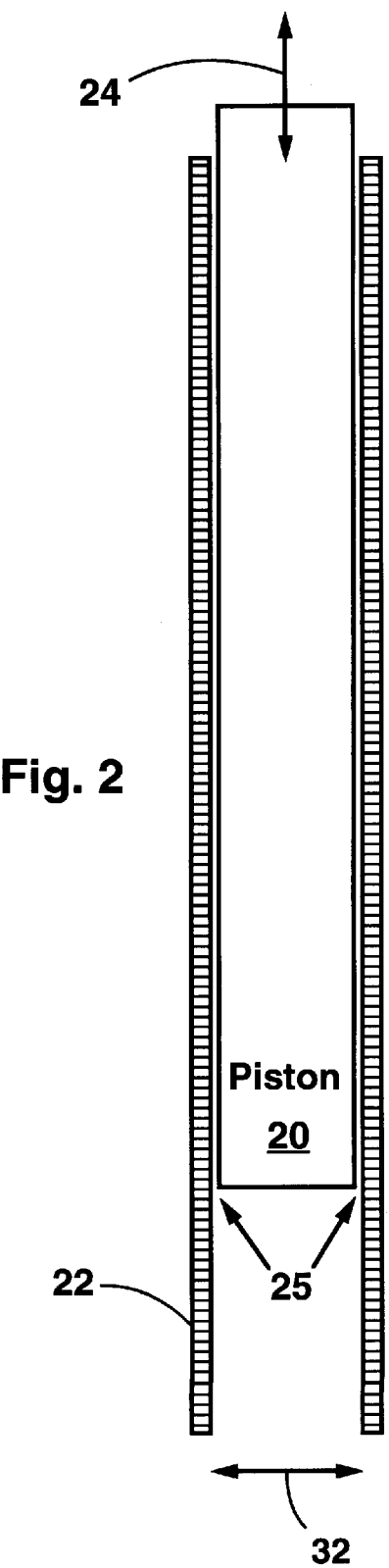
Fig. 1
Fig. 2

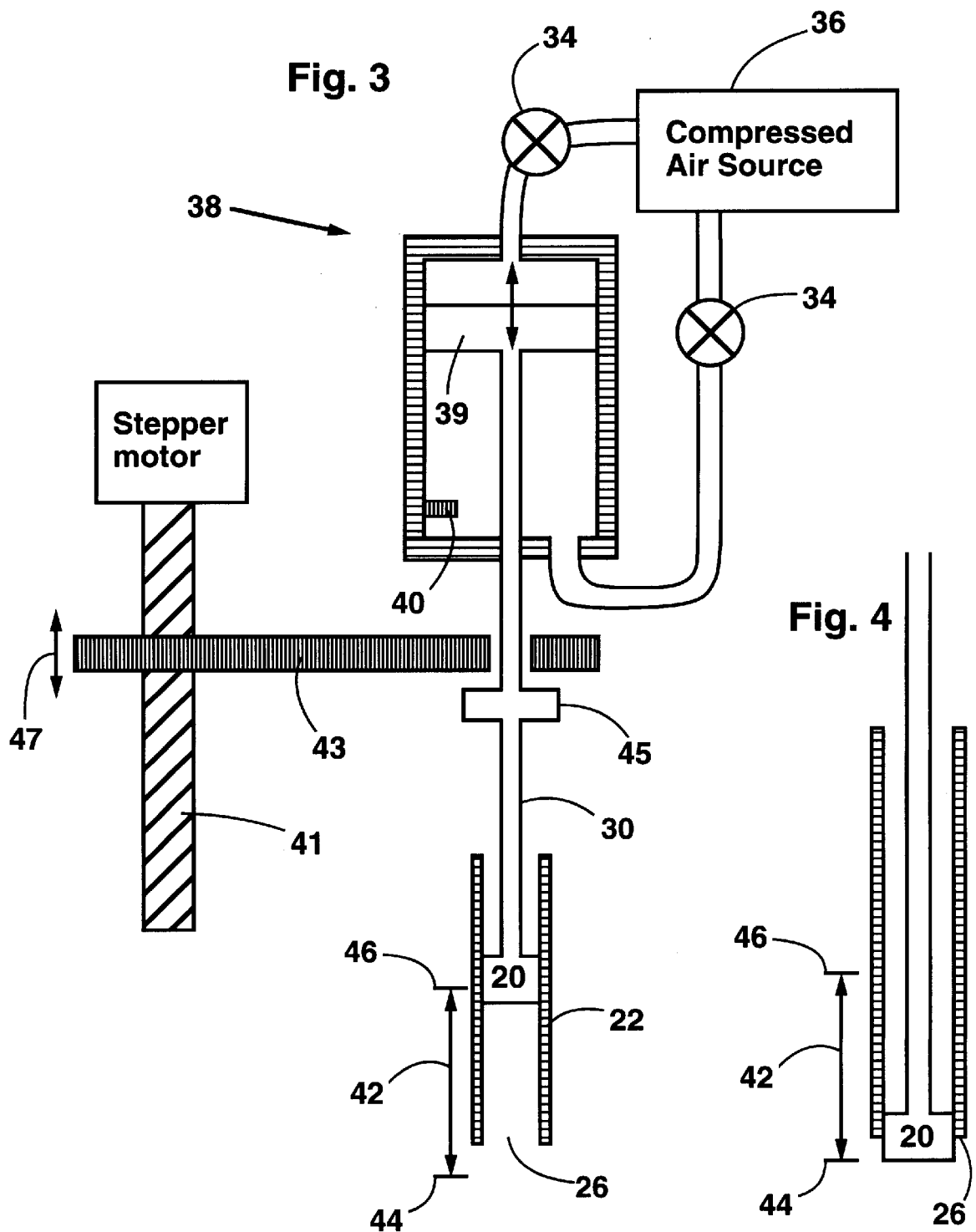

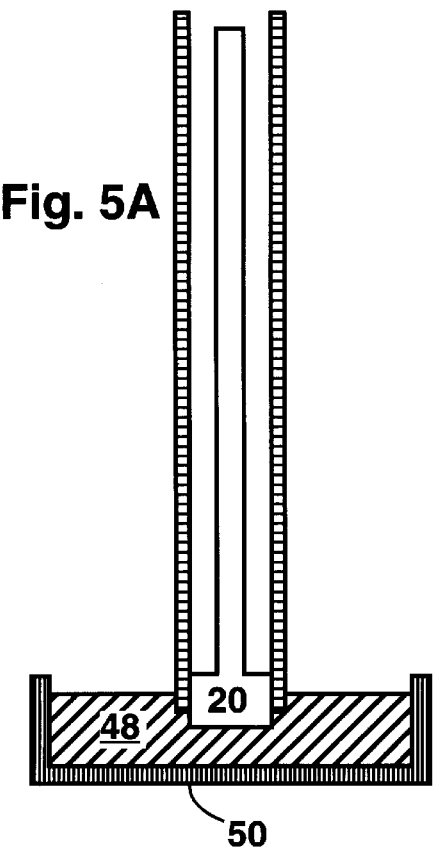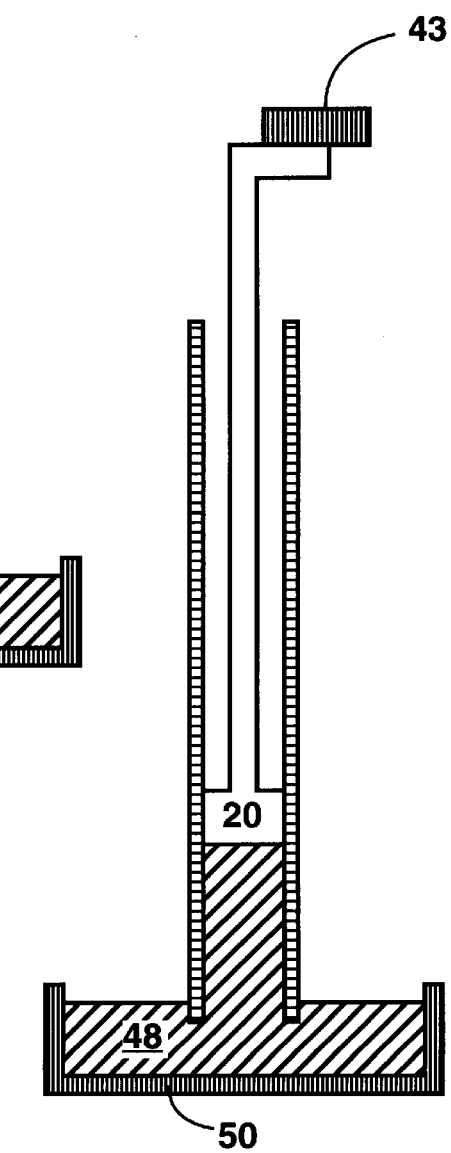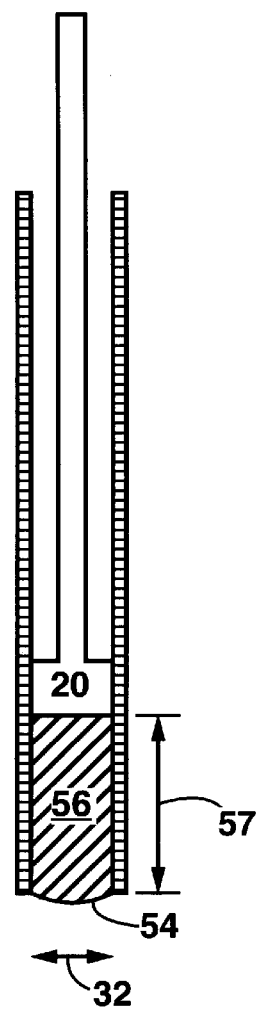

Fig. 7
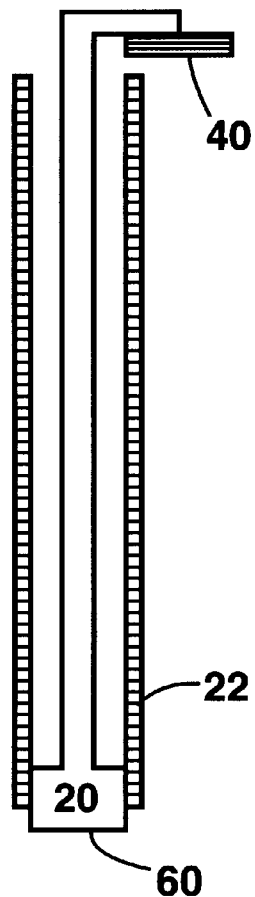
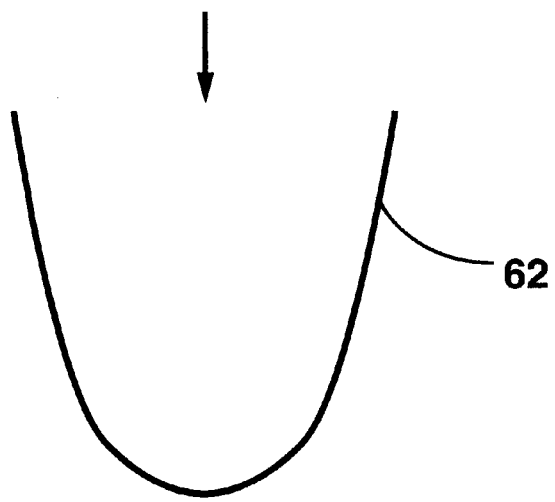

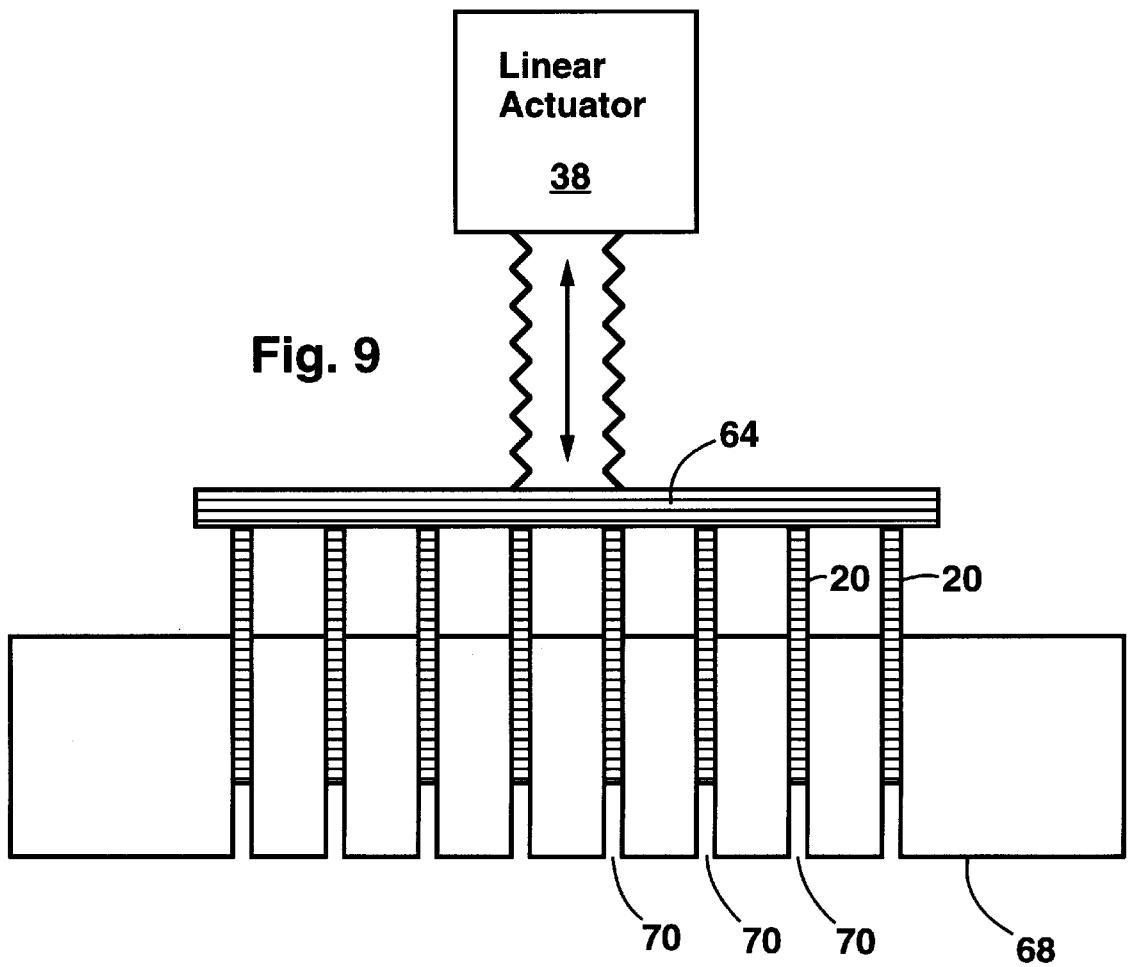
Fig. 9
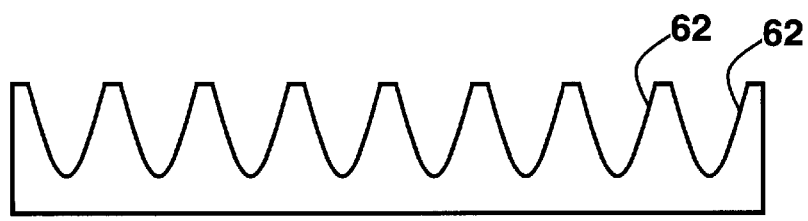

DEVICE FOR PROJECTILE DISPENSING OF SMALL VOLUME LIQUID SAMPLES

FIELD OF THE INVENTION

This invention relates generally to devices for the dispensing of microliter volumes of liquid samples. More specifically, it relates to the dispensing of small volumes of liquid using a positive displacement technique.

BACKGROUND OF THE INVENTION

The accurate dispensing of small volume liquid samples is of great importance in many industries, particularly the biotechnology industry. Often, large numbers of liquid samples must be analyzed or manufactured. In many such processes in the biotechnology industry, the reagents used are expensive biochemicals. Therefore, it is advantageous to perform the necessary procedures with small quantities of reagent. This has created a demand for machines which can rapidly, accurately and repeatably dispense such small quantities. Typically, sample volumes in the range of 0.1–10 microliters are of interest.

Many prior art devices dispense from a pipette tip which must contact the surface or test tube which receives the sample. In such a device a drop is formed at the pipette tip and then the tip is contacted to the receiving surface or test tube to deposit the drop. This contact method suffers from contamination problems because of the necessity of contact. Such contamination problems are increased if two or more reagents are to be mixed by depositing them in the same test tube. Also, the volume of the dispensed liquid depends upon the surface characteristics of the tip and receiving surface, adversely affecting the volume accuracy. Therefore, it would be an improvement in the art to use noncontact techniques to dispense liquid samples. Noncontact implies that the liquid must be ejected as a free droplet.

Piezoelectric droplet ejectors as commonly used in ink-jet printers are well known in the art and demonstrate a technique for noncontact dispensing of liquids. However, such devices are too large and expensive to use with standard 96-well trays as used in many machines. This would require 96 piezoelectric droplet ejectors. Another problem with this solution is that the largest quantity of liquid that can be ejected is so small that many applications would require hundreds or thousands of droplets. This is time-consuming and relatively inaccurate because the sample size error increases with the number of droplets. Piezoelectric ejectors also have problems relating to reliability and wear.

It is known in the art that a syringe-type positive displacement device comprising a piston inside a pipette can be used to eject liquid samples in a noncontact (projectile) fashion. It is also known that such a device must eject the liquid with a velocity sufficient to overcome the surface tension forces that tend to form the liquid into round droplets (if accurate noncontact dispensing is desired). The formation of round droplets makes it difficult to control the precise volume of liquid dispensed. U.S. Pat. No. 5,525,302 to Astle, for example, discloses an apparatus which can be used in a manner in which the velocity of the ejected liquid is great enough to exceed the surface tension forces. One problem with the device of Astle is that the piston cannot eject the entire quantity of sample liquid inside the pipette in a positive displacement fashion. The narrowing taper at the tip of the pipette prevents the piston from positively displacing and ejecting all the liquid. This is because the piston is not free to move beyond the end of the tube. It is possible to eject the entire quantity of sample liquid by including in the pipette an air bubble and/or a quantity of inert working fluid such as water. However, this considerably complicates the procedure for aspirating and ejecting liquids. Another problem with the Astle invention and tapered pipettes generally is that the taper complicates the relationship between piston position and volume displacement. An accurate, clear relationship between piston position and volume displacement is very important for the dispensing of accurate liquid volumes.

U.S. Pat. No. 3,934,585 to Maurice discloses a device for projectile dispensing of small volumes from a tube tip. However, this invention uses a tube with a tapered tip, i.e. with a reduced diameter toward the end. Therefore, this invention has the same disadvantages associated with tapered tips as described above.

Therefore, there exists a need for a device which can accurately, conveniently and rapidly dispense small volume liquid samples in a noncontact fashion. Further, it would be advantageous for the device to be able to eject all the liquid contained within its pipette in a positive displacement fashion. It would also be advantageous for the device to have an accurate, clear relationship between piston position and volume displacement. The device should be a positive displacement device to provide the accuracy inherent in positive displacement methods.

OBJECTS AND ADVANTAGES OF THE INVENTION

Accordingly, it is a primary object of the present invention to provide a device for the dispensing of small volume liquid samples that:

1) is noncontact, i.e., does not require physical contact between the dispensing device and the receiving surface or test well;
2) rapidly dispenses liquid samples of accurate, repeatable volume;
3) provides an accurate, simple relationship between piston position and volume displacement;
4) is relatively inexpensive;
5) can be interfaced with standard, 96-well (with 9-mm centers) test trays; and
6) can dispense liquids in the volume range of approximately 0.1–10 microliters.

SUMMARY OF THE INVENTION

These objects and advantages are attained by a piston disposed inside a linear tube. The linear tube has a constant inner cross section (size and shape) along its entire length. Preferably, the linear tube is cylindrical, in which case it has a constant inner diameter. The piston is free to move axially inside the tube and preferably forms a liquid-tight seal with the inside walls of the tube. The inner cross sectional area of the tube is selected according to the volume of sample liquid to be dispensed; smaller sample volumes require a smaller tube cross sectional area.

Since the tube has a uniform inner cross sectional area and shape, a simple calculation of area X distance yields the volume displacement when the piston is displaced by a certain distance. The displacement volume is directly proportional to the piston displacement distance.

The tube has an open end through which the sample liquid is ejected. The open end also aspirates liquid when then piston is pulled back. In other words, the open end is used for both 'sucking' and 'spitting'. The open end of the tube is not tapered, but maintains the uniform inner cross section. This allows the piston to move out beyond the end of the tube through the open end.

A driving means such as a pneumatic actuator or solenoid is used to move the piston inside the linear tube. The driving means must be able to move the piston at a certain minimum velocity. The minimum velocity is determined by the type of liquid dispensed (its surface tension and adhesion characteristics) and the materials comprising the piston and linear tube. The piston velocity is selected such that the sample liquid is ejected from the tube end at a velocity great enough to render negligible the surface tension forces which tend to form the liquid sample into droplets.

The piston and sample liquid will need to be pulled back into the tube a distance before dispensing in order to provide the piston with a 'running start' when ejecting a sample. This is because the sample liquid must exit the open tube end with a minimum velocity.

The tubes of the present invention have a small diameter which allows for accurate metering of the sample liquid. A cylindrical tube having an inner diameter of 0.48 millimeters, for example, has a volume displacement of 1.81 microliters per centimeter of piston displacement. Thus, the volume of liquid dispensed can be accurately determined by accurately positioning the piston inside the tube. Of course, there exist many well known techniques that can be used to accurately control the piston displacement.

DESCRIPTION OF THE FIGURES

FIG. 1 is a side view of a generalized version of the present invention.

FIG. 2 is a side view of an embodiment wherein the piston is a solid cylinder which does not form an airtight seal with the tube.

FIG. 3 shows how the piston can be controlled using a pneumatic linear actuator and stepper motor apparatus.

FIG. 4 shows the piston in an extended position beyond the open end of the tube.

FIGS. 5A, 5B, and 5C show how accurate sample volumes can be aspirated into the device.

FIG. 7 shows a liquid sample being ejected into a test tube.

FIG. 9 shows an alternative embodiment which can simultaneously eject 8 liquid samples into a row of 8 test tubes.

DETAILED DESCRIPTION

Figure 6A:
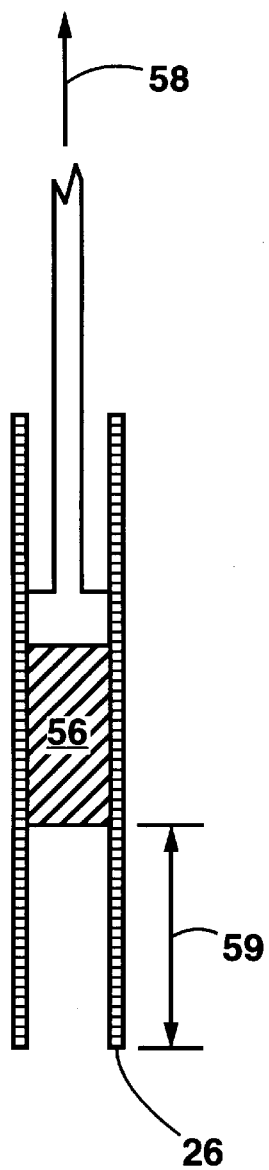
FIGS. 6A, 6B, 6C, and 6D show how samples are ejected.

A specific embodiment of the present invention is shown in FIG. 1. A piston 20 is disposed within a tube 22 and is free to slide in the direction of the arrow 24 shown. The tube 22 is preferably cylindrical. The cross sectional shape and size of the interior of the tube 22 must be uniform along its length such that the piston 20 maintains contact with the inner tube walls as it moves. The uniformity of the tube shape necessarily extends to an open end 26 of the tube 22. This allows the piston 20 to exit the tube 22 through the open end 26. Sampled liquids are aspirated (inhaled) and ejected through the open end 26.

The tube 22 is preferably made of glass or quartz, but any suitable, relatively inert material may be used. Glass is preferred in part because it is inexpensively available with an accurate, uniform inner diameter. This feature of glass tubing allows the piston 20 to form a relatively good seal against the inside walls of the tube 22. Other materials that the tube 22 may be fabricated from include polymers and stainless steel.

The piston 20 preferably has a head portion 28 which is made of an inert elastomer material and a shaft portion 30 which is made of a relatively rigid metal such as stainless steel or tungsten wire. An elastomer head portion 28 can provide a fluid-tight seal, as is well known in the art of syringe construction.

Alternatively, the piston 20 can be a single, cylindrical piece of metal, plastic, or glass which is sized to fit inside the tube 22 with little clearance. This possibility is shown in FIG. 2, which illustrates a gap 25 between the piston 20 and the inner wall of tube 22. In this embodiment, the piston 20 does not form a fluid-tight seal with the inner wail of tube 22. However, the gap 25 is thin and the distance of piston-tube contact long, so the fit between the piston 20 and tube 22 is nearly fluid tight. Further, the present invention is operated in such a fashion that sample liquid does not have enough time to leak through the gap 25.

The inner diameter 32 of the tube 22 is selected according to the volume of sample liquid to be dispensed. In a particular embodiment of the invention, the tube 22 has an inner diameter 32 of 0.48 millimeters. This results in a volume displacement of 1.81 microliters per centimeter of piston 20 travel. As is explained below, the piston volume displacement is equivalent to the volume of liquid dispensed. The volume displacement is proportional to the inner cross sectional area, so a smaller inner diameter tube 20 can be used to dispense smaller volumes. It is understood that an accurate movement of the piston 20 results in an accurate amount of piston volume displacement.

FIG. 3 illustrates a preferred apparatus which can be used to control the motions of the piston 20 inside the tube 22. A compressed air source 36 is connected to both sides of a pneumatic actuator 38 through two valves 34. The actuator piston 39 can be made to move up and down by controlling the valves 34. The actuator piston 39 is connected to the piston 20 inside the tube 22. The lower limit 44 of the piston range 42 is determined by a mechanical stop 40 inside the actuator 38. The upper limit 46 of the piston range 42 is determined by a movable stop plate 43 which blocks a collar 45 on the piston shaft 30. The stop plate 43 can be moved 47 vertically by means of a lead screw 41 attached to a stepper motor. Controlling the stepper motor thus controls the upper limit 46 of the piston range 42. Other means of accurately controlling the limits 44, 46 of piston 20 motion will be obvious to one skilled in the art of mechanical engineering. Also, other means of moving the piston 20 will be obvious. The apparatus of FIG. 3, for example, may further include a means for accurately sensing and controlling the piston 20 position electronically.

FIG. 4 illustrates a preferred feature of the present invention in which the bottom limit 44 is slightly past the open end 26 of the tube 22. This feature improves the ability of the piston 20 to eject all the aspirated liquid. The distance between the open end 26 and the top limit 46 determines the amount of piston volume displacement.

It will be obvious to one skilled in the art of mechanical design that there exist techniques other than the use of mechanical stops for assuring that the piston 20 has an accurately determined range 42 of motion.

FIGS. 5A, 5B, and 5C illustrate the process by which sample liquid 48 is aspirated into the tube 22. First, while the piston 20 is at the bottom limit 44 position, the open end 26 and piston 20 are partially submerged in a reservoir 50 containing sample liquid 48. Next, as illustrated in FIG. 5B, the piston 20 is pulled back a predetermined distance. This distance is determined by the stop plate 43 as shown in FIG.

3. Also preferably, the piston 20 is pulled back slowly. Slow movement of the piston 20 can be accomplished by slowly allowing compressed air into the pneumatic actuator 38 shown in FIG. 3. Removing the tube and piston assembly (FIG. 5C) from the reservoir 50 leaves an accurately determined volume of liquid 56 (the sample) remaining in the end of the tube 22. The volumetric error due to the curved liquid surface 54 is small because, for most liquids, the curvature is small as a result of the small inner diameter 32 of the tube 22.

The length 57 and cross sectional area of the sample liquid 56 determines the volume of the sample 56. For example, if the inner diameter 32 of the tube is 0.48 millimeters, then the volume of the sample 56 is 1.81 microliters per centimeter of sample liquid length 57. A sample 56 5 millimeters long will have a volume of 0.905 microliters. It will be obvious to one skilled in the art of liquid measurement how to select the inner diameter 32 and sample length 57 to produce a sample of a desired volume. It is understood that the present invention can be used to select sample volumes approximately in the range of 0.1–10 microliters by using tubes with different inner diameters and by aspirating samples 56 of different lengths.

FIGS. 6A–6D illustrate the method by which the liquid sample 56 is ejected from the tube 22. First, the liquid sample 56 is drawn further into the tube 22 by pulling 58 the piston 20 into the tube 22. This step provides a running start for the sample 56 to reach a minimum exit velocity before it reaches the end of the tube 26. More specifically, the distance 59 between the bottom edge of the sample 56 and the tube end 26 must be great enough to allow the sample to be accelerated to the minimum exit velocity before it reaches the end 26 of the tube 22.

Figure 6B:
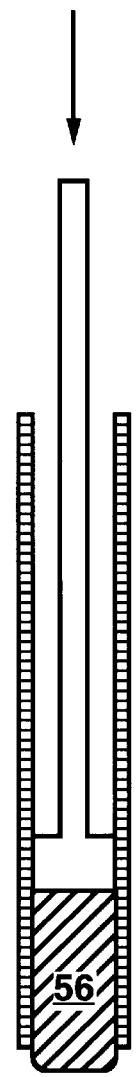
Figure 6C:
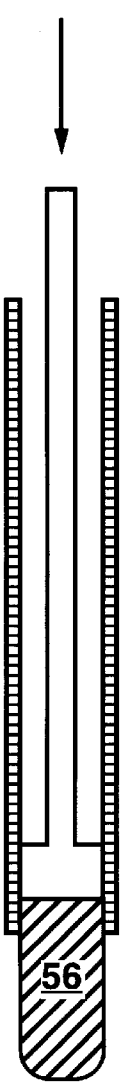
Figure 6D:
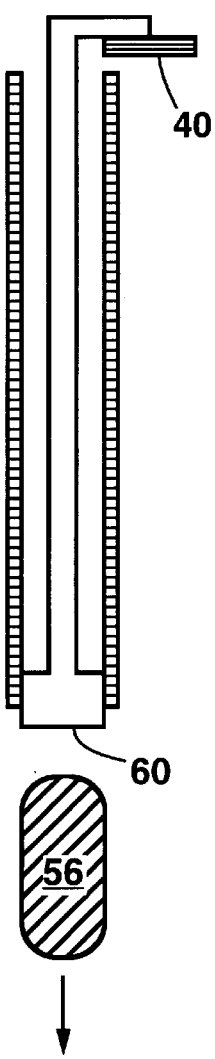

Next, as shown in FIGS. 6B and 6C, the piston 20 is rapidly accelerated downward, achieving the minimum exit velocity before the sample 56 reaches the open end 26. Finally, at the end of the delivery cycle shown in FIG. 6D, the piston 20 comes to a sudden stop slightly beyond the tube end 26, and the sample 56 continues as a flying cylinder of liquid 56. The sample 56 leaves the tube 22 approximately as a cylinder because its velocity is so high that surface tension forces do not have time to deform the sample 56 and are not great enough to overcome the sample inertia. This is an essential feature of the present invention. The piston 20 comes to a sudden stop of sufficient deceleration such that a droplet of the sample 56 cannot adhere to the endface 60 of the piston 20. The minimum exit velocity required for the entire sample 56 to be ejected depends upon the density and surface tension of the sample liquid 56 and on the wettability of the piston 20.

If the piston 20 is made of a material readily wettable by the sample liquid 56, then the sample 56 will adhere to it more strongly. This, in turn, results a higher required piston deceleration, which generally requires a higher piston velocity. This is undesirable in most situations. Teflon is a good material to use for the piston face 60 because it is relatively unwettable by many liquids, including water.

As an illustrative example, a sample of water can be successfully ejected from a 0.48 millimeter diameter glass tube with a teflon piston?? by providing an exit velocity of about 1.4 meters per second. It is expected that most water-based samples can be ejected using exit velocities in the approximate range of 1.2–1.6 meters per second. Minimum exit velocities for other liquids may need to be determined empirically.

The sudden stop of the piston is preferably provided by a mechanical stop 40 as shown in FIG. 3. The mechanical stop 40 is preferably made of a somewhat compliant material such as hard rubber such that the piston 20 bounces slightly at the end of the delivery cycle. A small bounce in the piston motion improves the ability of the piston 20 to eject all the sample liquid 56. In other words, a bounce helps prevent a droplet of sample liquid from adhering to the piston endface 60.

If the sample 56 is ejected too slowly (slower than the minimum exit velocity), then surface tension forces will cause the sample to form a droplet and the sample 56 will adhere to the open end 26 of the tube 22 as a droplet.

The piston 20 is preferably accelerated by means of a pneumatic linear actuator as shown in FIG. 3. Such actuators provide the smooth, even and powerful forces necessary for the present invention. Pneumatic linear actuators are very well known in the art. However, other linear actuators such as electromagnetic solenoids or spring-loaded devices may also be used.

Since the sample 56 mass is much smaller than the mass of the pneumatic actuator mechanism (actuator piston 39), the acceleration of the piston 20 during sample ejection will be relatively independent of sample mass. This implies that the running start distance 59 required will be independent of sample volume. The running start distance 59 in a particular device will only depend upon the piston acceleration and the required sample exit velocity. In the case of using a pneumatic actuator the piston acceleration can be controlled by changing the compressed air pressure.

FIG. 7 shows the present invention dispensing a liquid sample 56 into a test tube 62. Since the liquid sample is ejected from the dispenser of the present invention as a projectile, it may be aimed into a test tube 62 or test well of a 96-well tray. This feature means that the dispensing can be performed without any part of the dispenser (tube 22 or piston 20) contacting the test tube 62. Thus, the present invention provides a noncontact dispensing device.

It is an object of the present invention to provide a liquid sample dispenser which can be used with the standard 96-well trays commonly used in biochemical laboratory processes. Such an application requires that 96 tubes with 96 pistons be assembled to provide 96 liquid sample dispensers. The dispensers of the present invention are small enough to fit in a grid with 9 millimeter center-to-center distance as is standard in 96-well trays. The 96 dispensers can be individually controlled by 96 separate actuators, or may be driven by a single actuator such that they operate in unison.

Figure 8:
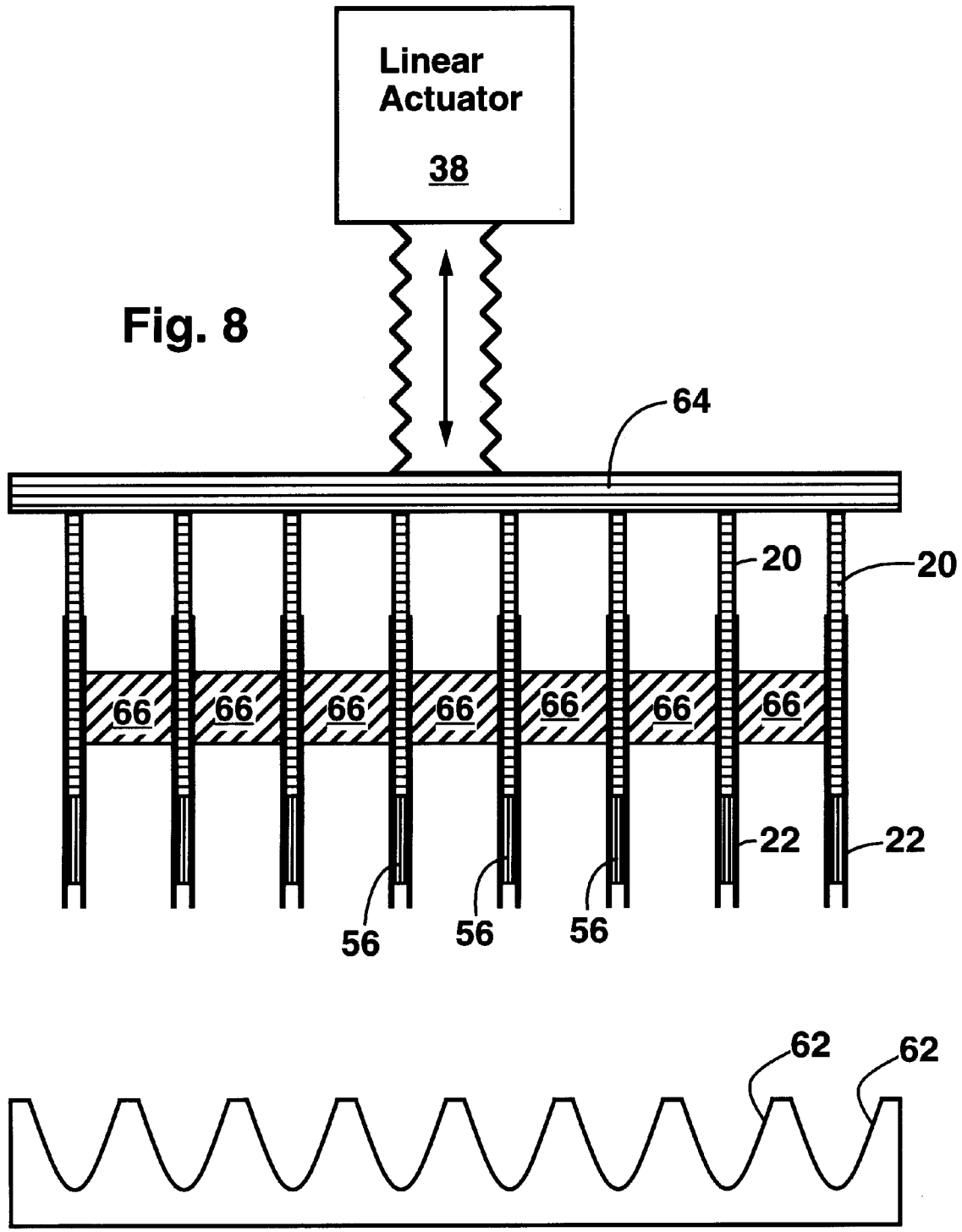
FIG. 8 shows a device which can simultaneously eject 8 liquid samples into a row of 8 test tubes.

FIG. 8 shows an embodiment designed for simultaneously ejecting 8 identical liquid samples 56 into 8 test tubes 62. Here, 8 pistons 20 are moved within 8 tubes 22 by a single linear actuator 38. The 8 pistons 20 are mounted to a common mechanical support 64 which is moved by the linear actuator 38. Similarly, 8 tubes are held by a common mechanical support 66. It is obvious that any number of dispensers can be operated in the fashion of FIG. 8 and that two dimensional arrays of dispensers can be constructed. Of course, mechanical stops can be used to provide an accurate range of motion for the pistons 20.

FIG. 9 shows an alternative embodiment of the present invention in which the multiple tubes 22 of FIG. 8 are replaced with a solid block of material 68 having parallel holes 70 of accurate, predetermined diameter. The pistons 20 are moved within the holes 70 by a linear actuator 38. The block 68 can be made of glass, plastic, metal or any suitable, inert material. This embodiment can provide a dispenser for a 96 well tray by drilling a grid of 96 holes with 9 mm centers in the block 68.

It will be clear to one skilled in the art that the above embodiment may be altered in many ways without departing from the scope of the invention. Accordingly, the scope of the invention should be determined by the following claims and their legal equivalents.

What is claimed is:

1. A device providing noncontact dispensing of a liquid sample, said device comprising:
   A) a linear tube having:
      1) an inner cross sectional shape that is uniform along the length of said tube,
      2) an inner cross sectional area sufficiently small so that the liquid sample is held in the linear tube by surface tension, and
      3) an open end;
   B) a movable piston disposed inside said linear tube such that said piston pushes said liquid sample out of said open end;
   C) a driving means for moving said piston towards said open end at a predetermined velocity,
   D) a means for rapidly decelerating said piston at the end of a delivery cycle,
   wherein said liquid sample is dispensed by accelerating said liquid sample to said predetermined velocity by pushing with said piston and then rapidly decelerating said piston at a rate sufficient to render negligible the surface tension forces on said liquid sample as said liquid sample is ejected from said open end.

2. The device of claim 1 wherein said tube has an inner cross sectional area in the range of approximately 0.1–3.0 square millimeters.

3. The device of claim 1 wherein said tube is cylindrical in shape.

4. The device of claim 1 wherein said driving means is a pneumatic actuator.

5. The device of claim 1 wherein said piston extends out of said open end at the end of said delivery cycle.

6. The device of claim 1 wherein said decelerating means causes said piston to bounce at the end of said delivery cycle.

7. The device of claim 1 wherein said piston head is comprised of a relatively unwettable material.

8. The device of claim 1 wherein said tube is comprised of a material selected from the group consisting of glass, quartz, stainless steel, and polyether ethyl ketone.

9. The device of claim 1 wherein said piston is a solid cylinder and does not form a liquid-tight seal with the inside surface of said tube.

10. The device of claim 1 wherein said piston forms a liquid-tight seal with the inside surface of said tube.

11. The device of claim 1 further comprising a movable stop plate for determining the volume of said sample liquid.

12. The device of claim 1 wherein said predetermined velocity is approximately in the range of 1.2–1.6 meters per second.

13. A device providing noncontact dispensing of a plurality of liquid samples, said device comprising:
   A) a plurality of parallel linear tubes, each tube having:
      1) an inner cross sectional shape that is uniform along the length of said tube,
      2) an inner cross sectional area sufficiently small so that the liquid sample is held in the linear tube by surface tension, and
      3) an open end;
   B) a movable piston disposed inside each said linear tube such that each said piston pushes each said liquid sample out of each said open end;
   C) a driving means for moving said pistons toward said open ends at a predetermined velocity,
   D) a means for rapidly decelerating said pistons at the end of a delivery cycle,
   wherein said liquid samples are dispensed by accelerating said liquid samples to said predetermined velocity by pushing with said pistons and then rapidly decelerating said pistons at a rate sufficient to render negligible the surface tension forces on said liquid samples as said liquid samples are ejected from said open ends.

14. The device of claim 13 wherein said tubes have an inner cross sectional area in the range of approximately 0.1–3.0 square millimeters.

15. The device of claim 13 wherein said tubes are cylindrical in shape.

16. The device of claim 13 wherein said driving means comprises at least one pneumatic actuator.

17. The device of claim 13 wherein said pistons extend out of said open ends at the end of a delivery cycle.

18. The device of claim 13 wherein said decelerating means causes said pistons to bounce at the end of said delivery cycle.

19. The device of claim 13 wherein said pistons are individually controllable.

20. The device of claim 13 wherein said pistons move in unison.

21. The device of claim 13 wherein said piston heads are comprised of a relatively unwettable material.

22. The device of claim 13 wherein said tubes are comprised of a material selected from the group consisting of glass, quartz, stainless steel, and polyether ether ketone.

23. The device of claim 13 wherein said pistons are solid cylinders and do not form liquid-tight seals with the inside surfaces of said tubes.

24. The device of claim 13 wherein said pistons form liquid-tight seals with the inside surfaces of said tubes.

25. The device of claim 13 wherein said parallel linear tubes comprise parallel holes formed in a solid block of material.

26. The device of claim 13 wherein said predetermined velocity is approximately in the range of 1.2–1.6 meters per second.

* * * * *